United States Patent [19]

Errico et al.

[11] Patent Number: 5,667,508
[45] Date of Patent: Sep. 16, 1997

[54] UNITARY LOCKING CAP FOR USE WITH A PEDICLE SCREW

[75] Inventors: Thomas J. Errico, Summit; James D. Ralph, Oakland; Steven Tatar, Montville, all of N.J.

[73] Assignee: Fastenetix, LLC, Summit, N.J.

[21] Appl. No.: 641,504

[22] Filed: May 1, 1996

[51] Int. Cl.$^6$ .................................................. A61B 17/86
[52] U.S. Cl. .................................................. 606/73; 606/61
[58] Field of Search .................................. 606/60, 61, 72, 606/73

[56] References Cited

U.S. PATENT DOCUMENTS

| | | | |
|---|---|---|---|
| 5,129,388 | 7/1992 | Vignaud et al. | 606/61 |
| 5,217,497 | 6/1993 | Mehdian | 623/17 |
| 5,261,912 | 11/1993 | Frigg | 606/61 |

Primary Examiner—Michael Buiz
Assistant Examiner—David O. Reip
Attorney, Agent, or Firm—Joseph P. Errico, Esq.

[57] ABSTRACT

A unitary locking cap mechanism, which is used with pedicle screws and other orthopaedic implant devices which couple bones to rods, includes rim and post portions which are rotationally freely coupled to one another to permit independent motion relative to one another. The rim element has a cylindrical body with an open end and a closed end; the closed end alternatively having a concentric hole defined by an inwardly directed flange. In one embodiment, the flange includes a series of slots, dividing into a plurality of wedge-shaped pie sections. In another embodiment, the sidewall of the cylindrical portion of the rim includes an annular recess. The post is a cylindrical shaft having surface elements at one end which provide for mutual engagement with the rim. These surface elements may be deflecting arms which seat into the annular recess of the rim, or an annular recess in the shaft into which the wedge-shaped pie sections of the flange portion may be resiliently snapped into. In an alternative embodiment, the shaft and the rim are coupled together through the concentric hole by a retaining ring which is placed around the shaft, in an annular recess therein, after the insertion of the shaft through the hole. Each embodiment are alternatively designed such that the post or the inner surface of the rim portions are threaded so that it can mate with a threading on the inner or outer upwardly extending, U-shaped channel forming, members of the heads of the pedicle screws.

8 Claims, 9 Drawing Sheets

UNITARY LOCKING CAP FOR USE WITH A PEDICLE SCREW

BACKGROUND OF THE INVENTION

1. Field of the Invention

This invention relates generally to a unitary locking cap device with secures a rod in the head portion of a pedicle screw, and more particularly to a locking cap having concentric post and outer cylindrical rim portions which are rotationally freely coupled with one portion being threaded and the other being smooth.

2. Description of the Prior Art

The spinal column is highly complex system of bones and connective tissues which houses and protects critical elements of the nervous system and the arterial and veinous bodies in close proximity thereto. In spite of these complexities, the spine is a highly flexible structure, capable of a high degree of curvature and twist through a wide range of motion.

Genetic or developmental irregularities, trauma, chronic stress, tumors, and disease, however, can result in spinal pathologies which either limit this range of motion, or which threaten the critical elements of the nervous system housed within the spinal column. A variety of systems have been disclosed in the art which achieve this immobilization by implanting artificial assemblies in or on the spinal column. The most widely utilized of these immobilzation assemblies, especially in the lumbar spine, are the posterior pedicle screw and rod assemblies. These assemblies consist of screws which are inserted into the pedicles and/or sacrum, and rods which are coupled to the heads of the screws. The heads of the screws have U-shaped receiving channels in either the top or sides thereof. In addition, a class of these devices includes screws which have head portions which are polyaxial inasmuch as the heads can be angulated with respect to the shaft. One such polyaxial pedicle screw is described in U.S. Ser. No. 08/559,196, entitled "A Polyaxial Locking Screw And Rod Coupling Element", filed Nov. 13, 1995. In the devices of this class, it is generally the case that the insertion of the rod in the U-shaped channel, and subsequent locking of the rod therein causes the head and the shaft to be locked in position relative to one another. The locking of the rod in the channel is accomplished by the application of a threaded nut onto the outer top of the U-shaped channel, and/or by the insertion of a threaded post downwardly between the upwardly extending members.

It has been recognized that if only one of the locking elements, i.e., the threaded nut on the outside of the channel, or the threaded post betweeen the upwardly extending members, is used, under normal loading of force, the upwardly extending members which form the U-shaped channel therebetween can deflect, thereby loosening the rod in the channel. (If the threaded nut is used, the members may deflect inwardly; if the threaded post is used, the members may deflect outwardly.)

A variety of solutions to this problem have been proposed, generally including a dual locking assembly having both an outer locking nut and an inner threaded post. For example, the device described in U.S. Pat. No. 5,443,467 to Biedermann, et al. teaches a locking mechanism which includes a threaded post which is inserted down the central axis of the U-shaped channel in head portion of the pedicle screw, and a threaded nut which is also applied to the outer surface of the channel portion of the head. The use of the Biedermann, et al. device is tedious inasmuch as the dual locking mechanisms must be applied simultaneously, for if one is positioned first, the second will not engage the threading (because of a forced deflection of the upwardly extending members outwardly by the threaded post, and inwardly by the threaded nut). In addition, the multiplicity of pieces which must be coordinated and accounted for during a given operation, as well as the size of such pieces, are considerable disadvantages of assemblies of the type discribed in the Beidermann, et al. reference.

It is, therefore, the principal object of the present invention to provide a unitary locking mechanism which securely retains the rod in the channel of the head of a pedicle screw.

In addition, it is an object of the present invention to provide such a locking mechanism which has only one element so as to reduce the number of pieces which must be utilized during a given surgical procedure.

Accordingly it is also an object of the present invention to provide a locking means which eliminates a class of small parts which are tedious to manipulate and are a risk of misplacement during a surgical procedure.

Other objects of the present invention not explicitly stated will be set forth and will be more clearly understood in conjunction with the descriptions of the preferred embodiments disclosed hereafter.

SUMMARY OF THE INVENTION

The preceding objects of the invention are achieved by the present invention which is a unitary locking cap for use with bone-to-rod coupling devices, and especially for use with rod stabilization and immobilization systems in the spine. (It shall be understood that a variety of orthopaedic implants may be contemplated which incorporate fixation devices which couple rods to bone, and it is anticipated that this unitary locking cap may be utilized with many of such devices.)

More particularly, the unitary locking cap has two distinct variations; the first variation being utilized with pedicle screws having a threading on the outer upper surfaces of the upwardly extending members which define the U-shaped channel; the second variation being used with screws having a threading on the interior of the upwardly extending members. Each of these variations includes a concentric pair of rotationally freely coupled central post and outer rim members. The various ways in which these elements may be coupled to provide rotationally independent movement is set forth herein as well.

More particularly, with respect to the outer rim member, the member comprises a cylindrical body having a first end and a second end. The first end is entirely open, having substantially the same diameter as the cylindrical body portion itself. The second end may be entirely closed or only have an inwardly directed annular flange portion which defines a concentric hole.

The post portion is a cylindrical element having a substantially uniform diameter along most of its axial length, from a first (bottom) end to a position which is below the second top end of the post. The top of the post may have a variety of different conformations which permit it to engage the second end of the outer rim member such that the two portions may be permanently coupled, but remain able to rotate relative to one another.

In a first embodiment, the interior surface of the cylindrical portion of the element has a threading which corresponds to the threading on the outer surfaces of the upwardly extending members of the head of the screw. Correspondingly, the central post is smooth, and is concentrically and coaxially mounted in the second end of the cylindrical body. The mutual means by which rotational freedom, but secure retention of the post within the rim portion is achieved includes an annular recess in the inner wall of the cylindrical body portion of the outer rim element and a plurality of outwardly extending spring deflecting arm elements which seat in the annular recess to permit the post to rotate, yet be retained and not removed.

Assembly of this embodiment is envisioned as occurring at the manufacturing site, where the cylindrical rim body portion and the post elements are made. The outwardly extending spring deflecting arm elements of the post portion are inwardly deflected as they seat in the threads of the inner wall of the body portion. The post portion is then rotated up and into the closed end of the body until the arms reach the annular recess. At this point, the arms resiliently snap into the recess, therein making removal impossible by virtue of the inability of the arms to reseat into the threads.

Upon the proper placement of a pedicle screw into the posterior of the patient's spine, and the seating of the rod in the U-shaped channel in the upper portion of the head of the pedicle screw, the unitary cap is placed over the upwardly extending members of the head, the concentric post providing self-centering for the cap. The engagement of the threads on the outer portion of the upwardly extending members and the inner wall of the cylindrical rim portion permits the cap to be advanced into contact with the rod. In alternative preferred aspects of this embodiment, either the post or the rim contacts the rod.

It shall be understood that this embodiment, which utilizes a plurality of deflecting arms of the post, and a corresponding annular recession on the inner surface of the rim member may be modified such that the post is threaded and the inner surface of the cylindrical rim portion is smooth. In such a modified design, the second end of the rim portion would have to be of the type which included a concentric hole, such that the post could be easily rotated and threadably advanced independently from the rim. In addition, the assembly of the device would have to provide a means for deflecting the arms inwardly during insertion such that they may snap into the annular recess.

In a second aspect, the present invention the second end of the outer rim portion must include the concentric hole. The diameter of the hole is approximately equal to that of the post portion. The annular flange of the second end of the rim portion further includes radial slots, thereby dividing the rim into pie-shaped wedge sections. These radial slots permit the concentric hole to be expanded and contracted via deflection of the flanges.

The post portion in this embodiment has a generally cylindrical shape having first and second ends, with a small annular recess formed in the side wall near the second end. The second end of the post has a thickened diameter which is substantially larger than the concentric hole so that the post does not readily fall through the hole. The diameter of the shaft of the post is also larger, but not by as much as the thickened second end, than the undeflected diameter of the concentric hole in the second end of the rim portion, however, the diameter of the annular recession in the post is smaller than this undeflected hole. Therefore, by deflecting the flanges initially, it is possible to insert the post through the concentric hole until the slotted flange wedges snap into the annular recess. As above, this coupling permits the post and the rim to rotate independently and freely of one another.

It, again, shall be understood that this aspect of the invention may be modified in the alternative to permit the post or the inner surface of the rim to have a threading.

In a third aspect, the present invention comprises a rim portion which includes the inwardly directed flange defining a concentric hole in the second end, but without the slots as described with respect to the second aspect above. As above, the second end of the post portion is thickened, however, the diameter of the shaft is less that the diameter of the concentric hole. Still, the shaft includes an annular recession near the thickened second end thereof. This annular recession is provided to receive and retain a snap-ring (an annular element which includes a single slot such that it may expand or contract upon the application of a radial force).

Assembly of this device includes insertion of the post through the concentric hole until the thickened second end seats against the lip of the concentric hole. A retaining snap-ring is then expanded and advanced up the shaft of the post portion from the first end thereof until it resiliently snaps into the annular recession in the post. The outer diameter of the snap-ring is larger than the diameter of the concentric hole, such that the post cannot be either advanced or retracted from the hole, but each portion remains rotationally free relative to the other.

As with both of the first two aspects, this assembly may be modified, alternatively, to have a threaded post or threaded interior surface of the rim portion.

BRIEF DESCRIPTION OF THE FIGURES

FIG. 4 is an assembled view of the embodiment of the unitary locking cap device of the present invention which includes the rim and post portions shown in FIGS. 2, 3a, and 3b, shown mounted to the head of the pedicle screw shown in FIG. 1a.

FIGS. 5a and 5b are side cross-section and top views, respectively, of the rim portion which is an aspect of another embodiment of the present invention.

DETAILED DESCRIPTION OF THE PREFERRED EMBODIMENT

While the present invention will be described more fully hereinafter with reference to the accompanying drawings, in which particular embodiments are shown, it is to be understood at the outset that persons skilled in the art may modify the invention herein described while achieving the functions and results of this invention. Accordingly, the descriptions which follow are to be understood as illustrative and exemplary of specific structures, aspects and features within the broad scope of the present invention and not as limiting of such broad scope.

Figure 1A:
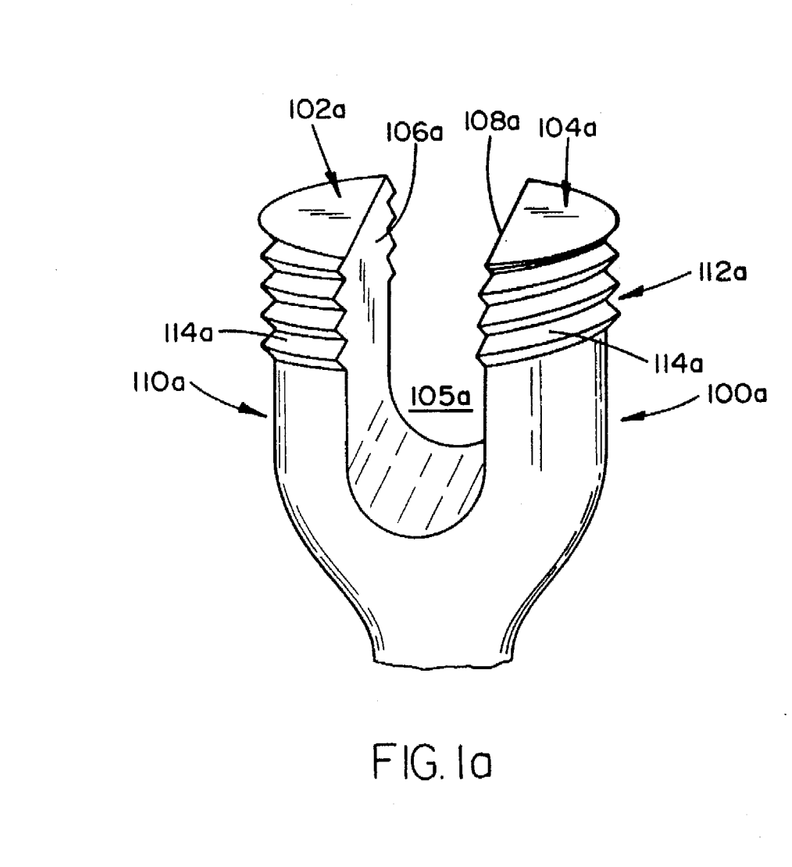
FIGS. 1a and 1b are side perspective views of the heads of pedicle screws having threading on the outer and inner surfaces, respectively, of the upwardly extending, U-shaped channel defining, members.
Figure 1B:
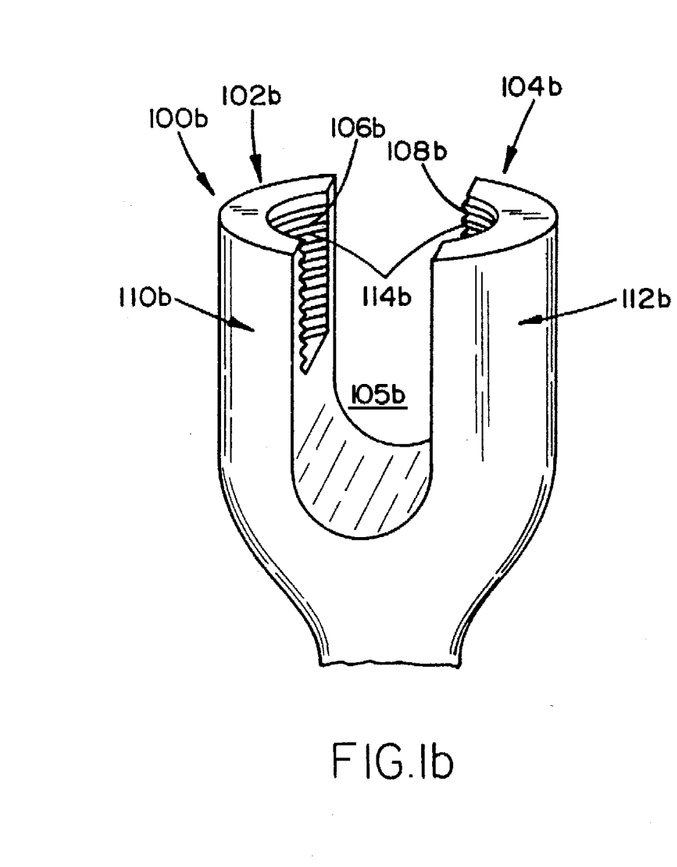

Referring first to FIGS. 1a and 1b, however, it is instructive, for understanding the function and utility of the present invention, in its various embodiments, to describe the corresponding variance in the upper conformation of pedicle screws with which this invention may be used. More specifically, with reference to FIG. 1a, there is shown the head of a pedicle screw 100a which includes a pair of upwardly extending members 102a,104a, which define therebetween a U-shaped channel 105a. A rod of a posterior spinal implant apparatus is ideally seated in this channel 105a and is locked therein by a locking nut (not shown). The upwardly extending members 102a,104b are semi-circular in cross-section; mutually defining two parts of an incomplete circle (the incomplete middle portion being the channel). The interior surfaces 106a,108a of the upwardly extending members 102a,104a are shown as being straight and mutually parallel, however, it shall be understood that the only requirements of the interior surfaces 106a,108a is that they be smooth and sufficiently spaced apart to receive the rod. The exterior surfaces 110a,112a of the upwardly extending members 102a,104a have a threading 114a thereon for receiving the locking nut for securing the rod in the channel (the locking nut preferably being the unitary locking cap of the present invention).

With reference to FIG. 1b, a second and alternative head of a pedicle screw 100b is described. The head of this second pedicle screw 100b is similar to the first 100a inasmuch as it has upwardly extending members 102b,104b which define a rod receiving channel 105b therebetween. The outer cross-sectional conformation of these members 102b,104b defines a partial circle as in the first pedicle screw, as well, however the outer surfaces 110b,112b of the members 102b,104b are smooth, and do not include a threading. Conversely, the inner surfaces 106b,108b of this pedicle screw 100b are curvate and threaded, mutually defining an incomplete circle (with the channel between the two members dividing the circle). The threading 114b in the interior surfaces is designed to receive a threaded post, as will be set forth more fully hereinbelow with respect to the second embodiment.

Figure 2:
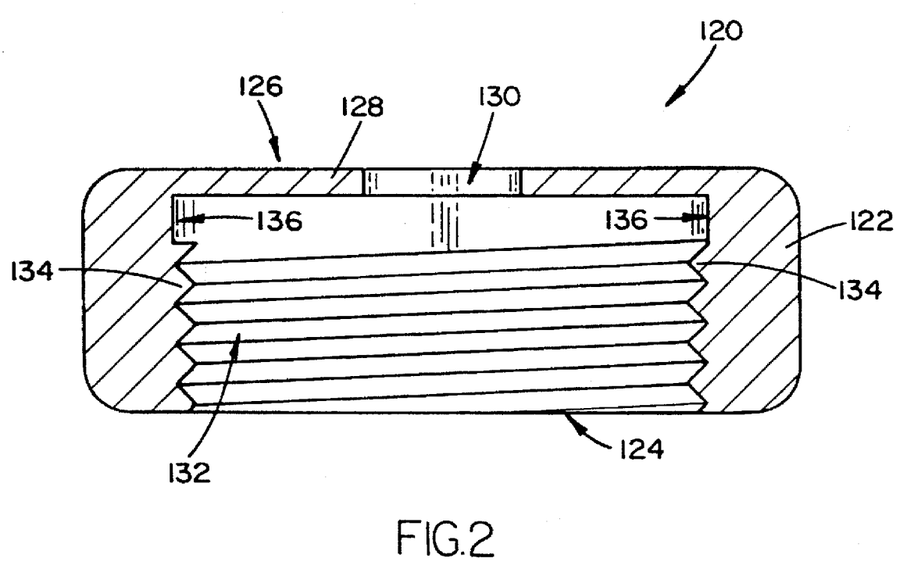
FIG. 2 is a side cross-section view the rim portion which is an aspect of one embodiment of the present invention.

Referring now to FIG. 2, however, the rim portion 120 of a first embodiment of the present invention is shown in a side cross-section view. This embodiment shall be understood to be used for securing rods in the receiving channels of pedicle screws of the type shown in FIG. 1a (with the threading on the outer surfaces of the upwardly extending members). More specifically, with respect to the rim portion 120, the element has a generally cylindrical body 122 which has a first open end 124 and a second semi-closed end 126. The second end 126 is defined by an inwardly directed annular flange 128 which in turn defines a concentric hole 130 through the end (hereinafter referred to as the top 126 of the rim portion). The inner surface wall 132 of the cylindrical body 122 includes a threading 134 which is engageable with the threading 114a of a pedicle screw 100a of the type shown in FIG. 1a. This threading 134 terminates at an axial distance which is spaced from the semi-closed end 126 of the rim portion 120. This unthreaded region includes an annular recession 136.

Figure 3A:
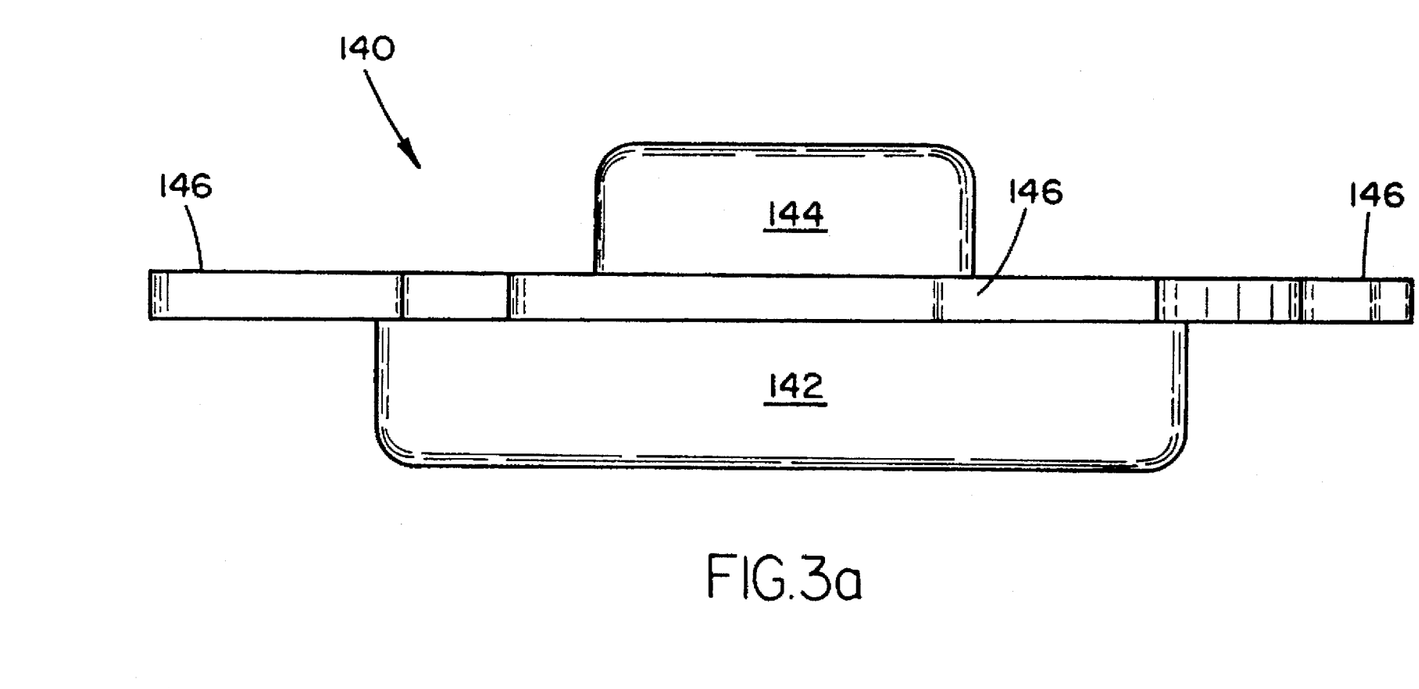
FIGS. 3a and 3b are side and top views, respectively, of the post portion which is an aspect of one embodiment of the present invention.
Figure 3B:
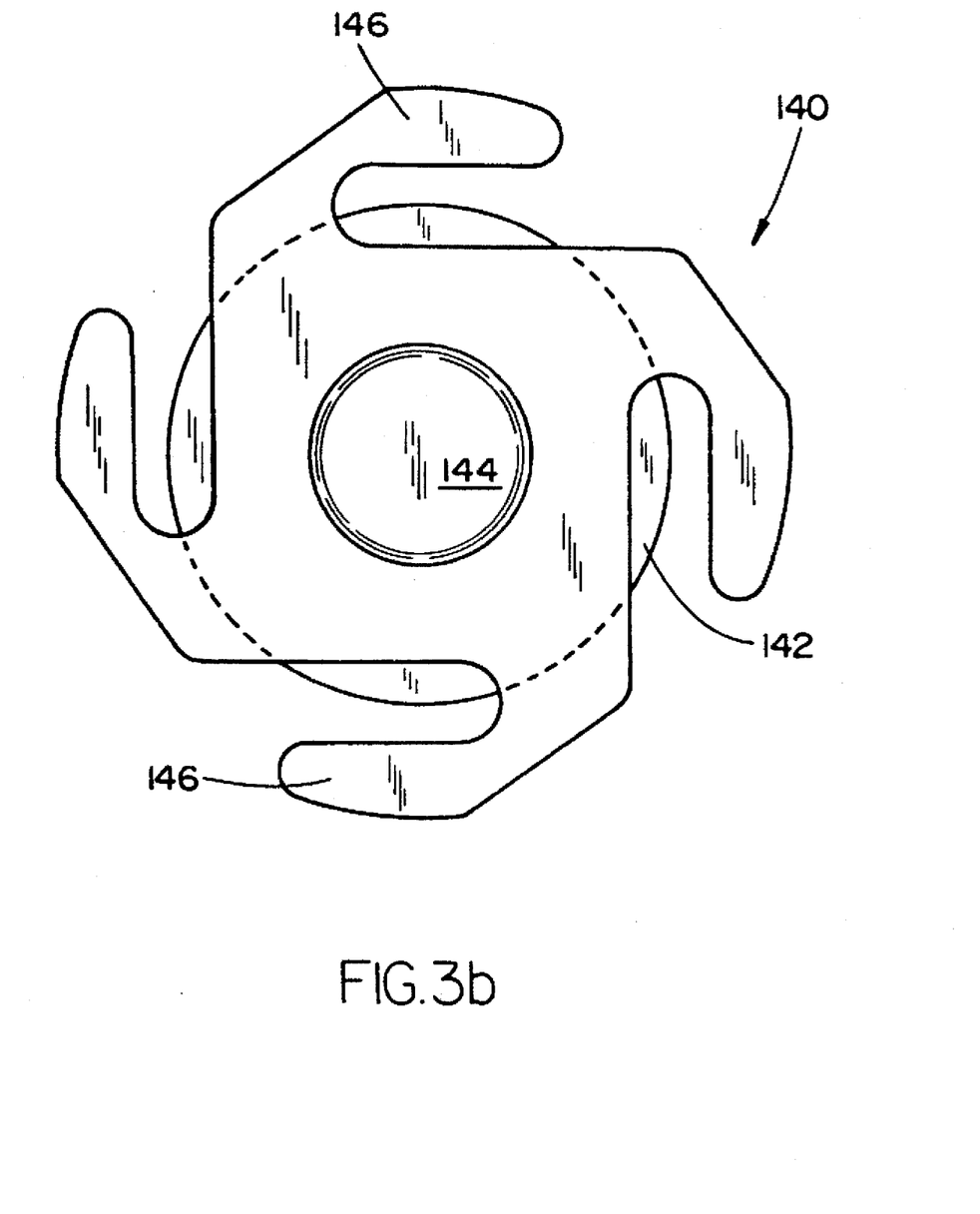

Referring now to FIGS. 3a and 3b, the post portion 140 of this embodiment of the present invention is shown in side and top views, respectively. The post portion 140 includes a cylindrical shaped body having a bottom section 142 which is wider than the top section 144 thereof. The bottom section 142 has a diameter which is substantially equal to the spacing between the upwardly extending members 102a, 104a of the pedicle screw 100a with which it is utilized. (As described above, the purpose of the post portion 140 is to prevent the upwardly extending members 102a,104a from deflecting inward, thereby permitting a loosening of the threaded locking mechanism from the members.) The top section 144 has a diameter which is slightly less than the concentric hole 130 in the top 126 of the rim portion 120. This top section 144 is provided to seat in the concentric hole 130 so as to self-center the post in the rim.

The post portion 140 further includes a plurality of deflecting arms 146 which extend radially outward from uppermost extent of the bottom section 142 (at the interface of the top and bottom sections 144,142, respectively). The deflecting arms extend outward to a diameter which permits them to engage the threading 134 of the rim portion 120 if deflected inwardly slightly. Therefore, during insertion, the arms 146 are deflected inward and the post 140 is threaded upwardly into the rim 120 from the bottom 124.

Once the post 140 has been threaded upwardly to the point where the arms reach the annular recess 136, the arms 146 spring back into their undeflected conformation, therein seating the post within the rim securely. Inasmuch as there is no means to redeflect the arms 146 inwardly so as to reengage the threading 134, the post 140 is securely retained in the rim 120. However, becuase the diameter of the annular recess is slightly larger than the undeflected diameter of the arms 146, the post 140 is free to rotate within the rim 120, thus allowing the post to remain motionless as the combined cap assembly is threaded onto the pedicle screw 100a.

Figure 4:
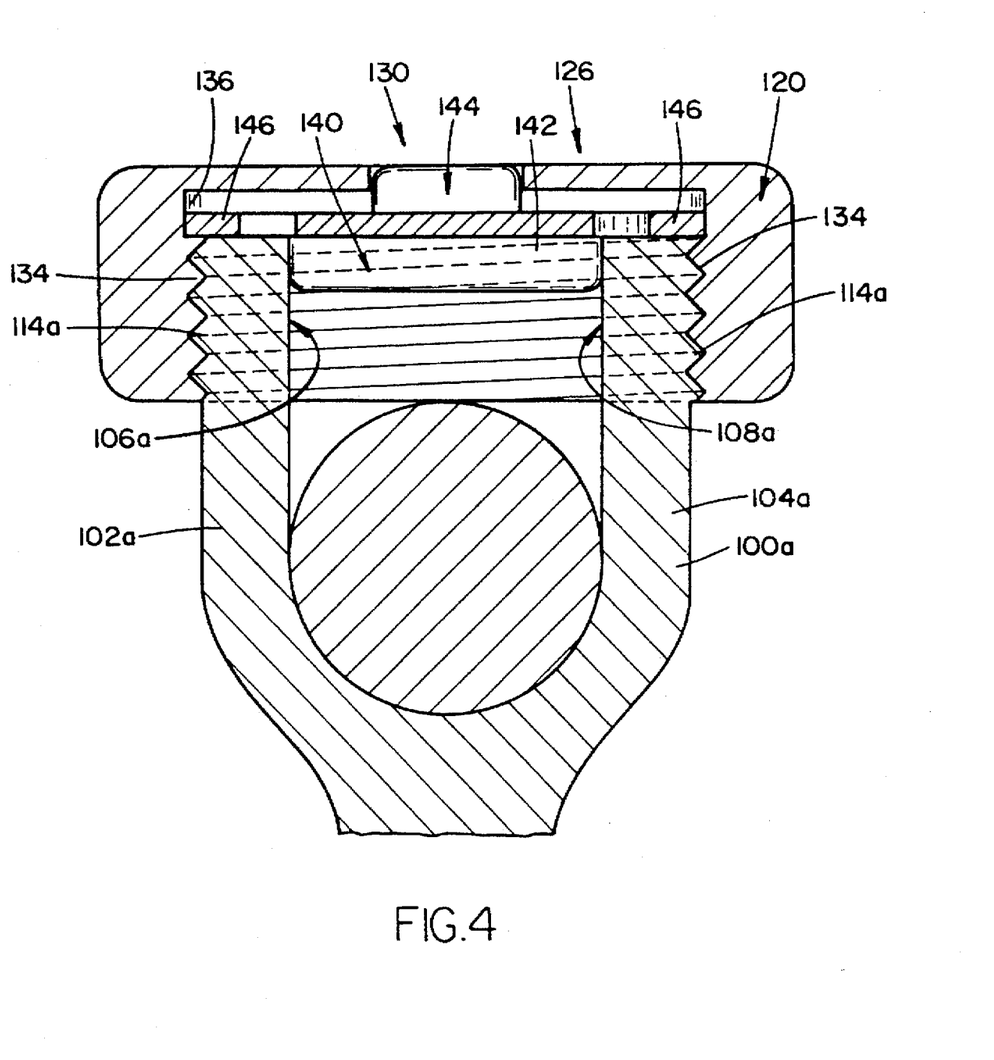

More particularly, with reference to FIG. 4, in which the unitary cap assembly is shown mounted to the top of the pedicle screw head 100a shown in FIG. 1a, the assembly of this embodiment is described. The post portion 140 is inserted into the rim portion 120 by threading the arms 146 of the post along the threading 114a of the inner surface of the rim. The post portion is ultimately retained within the rim by engagement of the arms 146 of the post seating in the annular recess 136 of the rim. This insertion process is ideally carried out at the manufacturing site such that the surgeon and operating room staff is relieved of the burden of assembling the unitary cap either pre-operatively, or during the operation.

The unitary cap is then introduced over the upwardly extending members 102a,104a of the pedicle screw head 100a. The inner threading 134 of the rim engages the threading 114a on the outer surfaces of the members (it being understood that the outer surface of the rim portion 120 has a conformation which permits its engagement by a wrench or other nut tightening means), and the bottom section 142 of the post 140 engages the smooth inner surfaces 106a,108a of the members 102a,104a. The members are thereby locked in place such that they may not deflect inwardly and the bottom of the rim portion 120 presses against the rod 75.

Figure 5B:
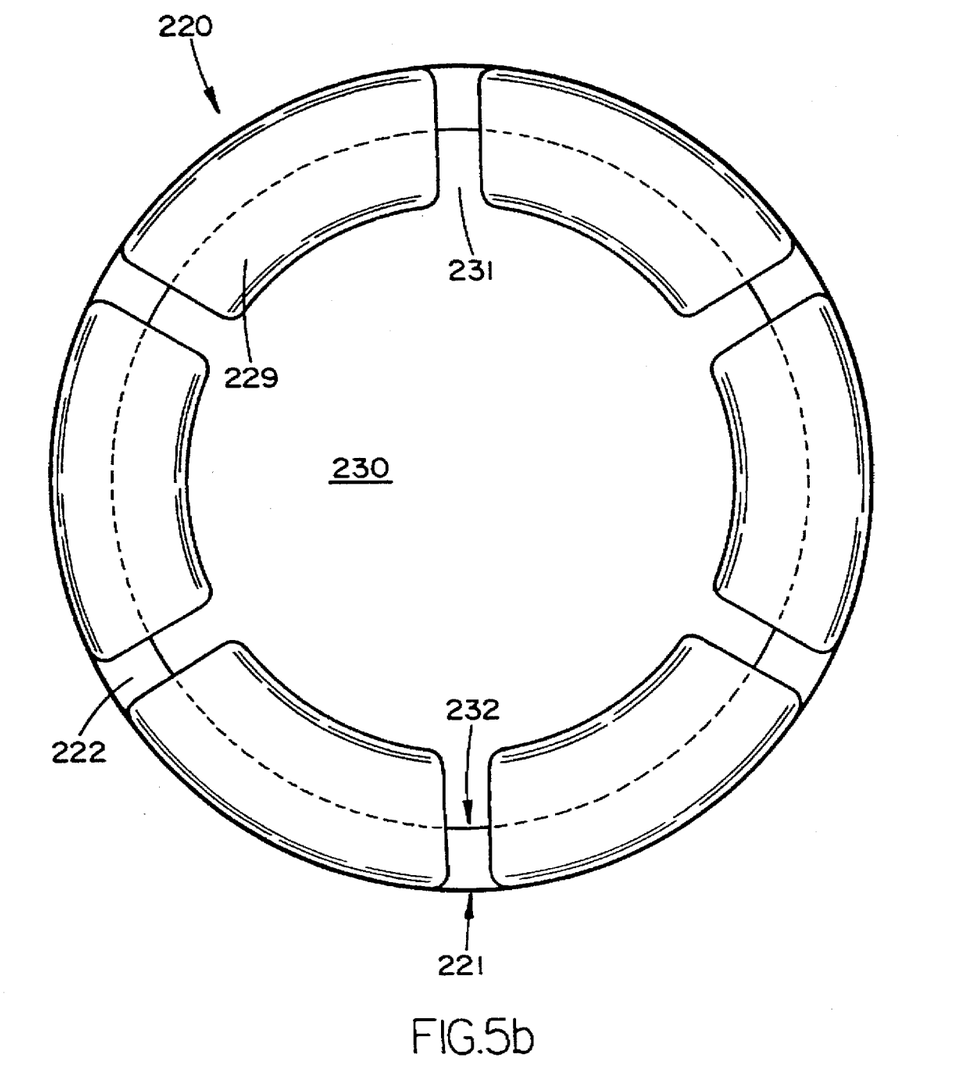

Referring now to FIGS. 5a and 5b, the rim portion of a second embodiment of the present invention is shown in side and top views, respectively. This embodiment is illustrated in a variation which is used with pedicle screw heads 100b having a threading 114b on the interior surfaces 106b,108b of the upwardly extending members 102b,104b. More specifically, with respect to the rim portion 220 of this embodiment, it comprises a generally cylindrical body 222 having smooth interior and exterior surfaces 232,221, respectively. The bottom end 224 is open; the top end 226 including an inward and upwardly extending flange 228 which defines a concentric hole 230 in the top 226. This flange 228 includes radial slots 231 such that it comprises pie-shaped wedges 229. The cylindrical body 222 is has a thinned sidewall thickness at its circumferential junction 223 with the flange 228. This thinned sidewall and the radial slots 231 in the flange permit the pie-shaped wedges 229 of the flange 228 to deflect so that the concentric hole 230 may expand or contract upon the application of a force upward or downward, respectively.

Figure 6:
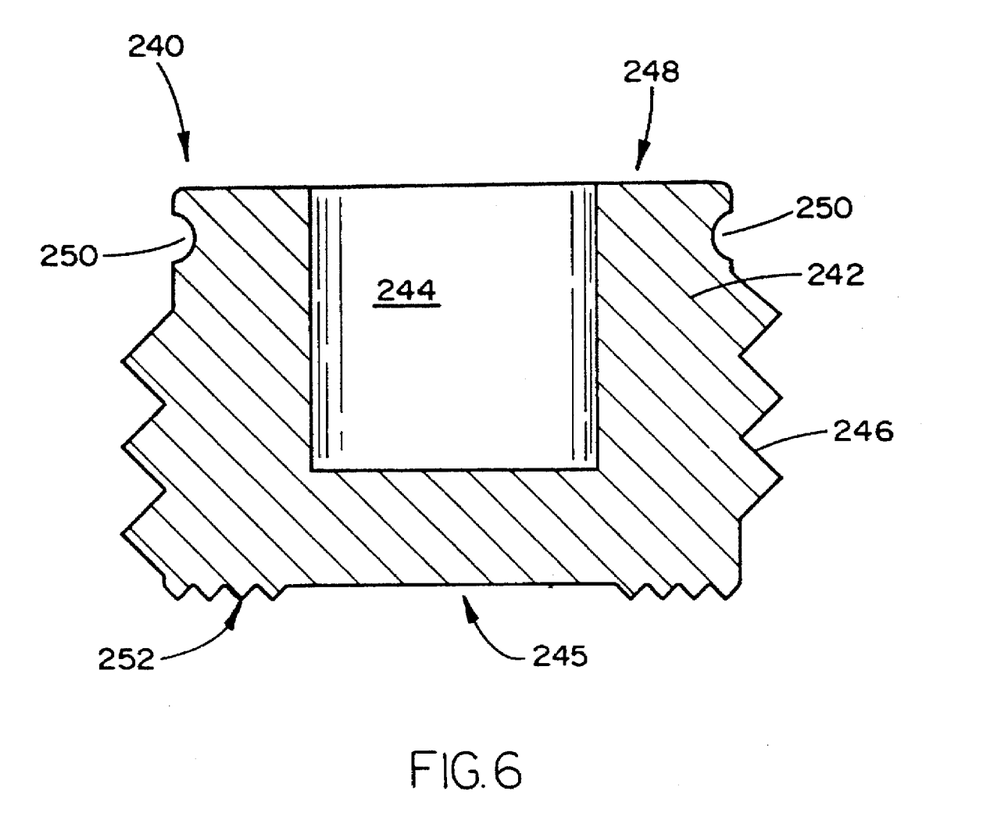
FIG. 6 is a side view of the post portion which is an aspect of another embodiment of the present invention.

Referring now to FIG. 6, the post portion 240 of this embodiment is shown in a side cross-section view. The post portion 240 comprises a cylindrical body 242 having an axial bore 244 extending down from the top 248 thereof which is designed to receive a screwdriving tool for selectively rotating the post. The external conformation of the post 240 includes a threading 246 extending from the bottom 245 thereof to a point axially spaced from the top 248 of the post. In this axial space between the terminus of the threading and the top 248, the post 240 further includes an annular recess 250. The exterior diameter of the post is larger than the undeflected diameter of the concentric hole 230 formed by the pie-shaped wedges of the flange 228 of the rim. The diameter of the annualr recess 250, however, is smaller than the undeflected diameter of the hole 230. The bottom 245 of the post is shown in this preferred embodiment as having a plurality of gripping ribs 252 which are provided for securely gripping the rod which it is to engage.

The post portion 240 of this embodiment is coupled to the rim portion 220 by upwardly deflecting pie-shaped wedges 229 of the flange 228 of the rim and inserting the top 248 of the post through the hole 230. Releasing the wedges 229 such that they snap into the annular recess 250 of the post, the post 240 and the rim 220 are coupled together inasmuch as they are co-xaially mated, but each remains rotationally independent and able to spin relative to the other.

(It shall be understood that in a variation of this embodiment, a retaining snap-ring may be seated in the annular recess 250 rather than the flange 228. In such an embodiment the diameter of the hole 230 would be larger than the diameter of the upper portion of the post such that the retaining ring would hold the post in the rim, not the engagement of the flange in the annular recess.)

Figure 7:
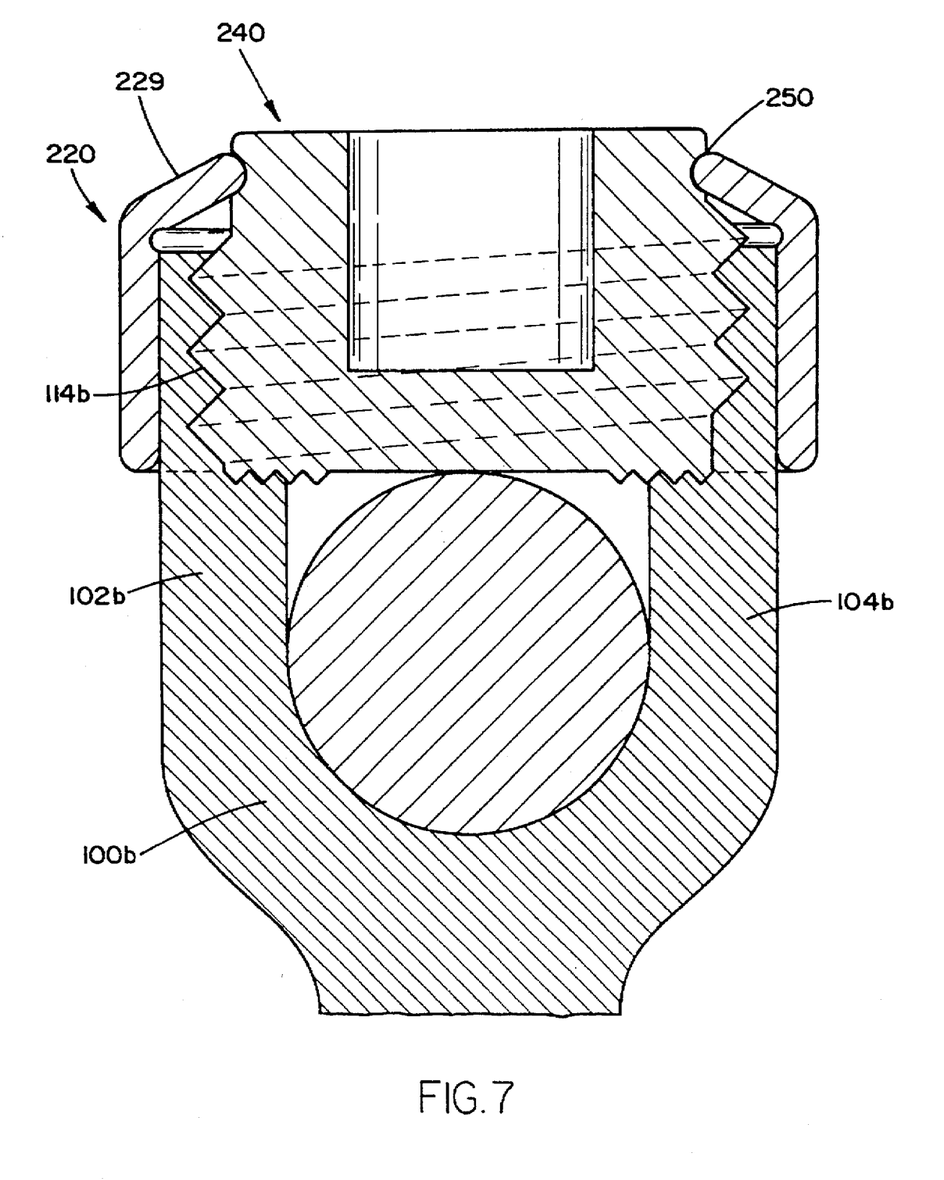
FIG. 7 is an assembled view of the embodiment of the unitary locking cap device of the present invention which includes the rim and post portions shown in FIGS. 5a, 5b, and 6, shown mounted to the head of the pedicle screw shown in FIG. 1b.

Referring now to FIG. 7, the fully assembled unitary cap of this embodiment is shown having been mated to the top of a pedicle screw 100b of the type shown in FIG. 1b. Once the post and rim portions, 240,220, respectively, have been mated as described above (preferably at the manufacturing site, rather than in the hospital environment), the surgeon simply places the unitary cap assembly over the upwardly extending members 102b,104b and threadably advances the post portion along the inner threading 114b of the screw head. The downward force applied by the post causes the rim portion to advance downward along the smooth exterior of the upwardly extending arms 102b,104b. This downward force also causes the wedges 229 of the flange 228 to deflect downward slightly, into the annular recess 250, further securing the rim 220 and post 240 and the rod 75 between the extending arms.

While there has been described and illustrated embodiments of a unitary locking cap assembly for use with pedicle screws in posterior spinal rod implantation apparatus (or other rod securing apparatus), it will be apparent to those skilled in the art that variations and modifications are possible without deviating from the broad spirit and principle of the present invention. The present invention shall, therefore, be limited solely by the scope of the claims appended hereto.

We claim:

1. A unitary locking cap for locking a rod in a rod receiving channel defined between a pair of upwardly extending members of an orthopaedic implant apparatus, said upwardly extending members each having mutually defined exterior and interior surfaces a threading on one of said exterior and interior surfaces, comprising:

a cylindrical body having a sidewall having inner and outer surfaces, said inner surface including an annular recess, a first end, which is open, and a second end, said body being mountable around the mutually defined exterior surfaces of said pair of upwardly extending members;

a post member which is positionable between said mutually defined interior surfaces of said pair of upwardly extending members, said post member including a plurality of deflecting arms extending radially therefrom which seat in the annular recess of said cylindrical body such that the post and the cylindrical body may rotate independently, but such that the post may not be removed;

a corresponding threading for engaging the threading on the upwardly extending members.

2. The assembly as set forth in claim 1, wherein said threading on said upwardly extending members is provided on exterior surfaces thereof and wherein said corresponding threading for engaging this threading on the exterior surfaces of the upwardly extending members is provided on the inner surface of said cylindrical body.

3. The assembly as set forth in claim 1, wherein said threading on said upwardly extending members is provided on interior surfaces thereof and wherein said corresponding threading for engaging this threading on the interior surfaces of the upwardly extending members is provided on the post.

4. A unitary locking cap for locking a rod in a rod receiving channel defined between a pair of upwardly extending members of an orthopaedic implant apparatus, said upwardly extending members each having mutually defined exterior and interior surfaces a threading on one of said exterior and interior surfaces, comprising:

a cylindrical body having a sidewall having inner and outer surfaces, a first end, which is open, and a second end, said second end including an inwardly directed flange which comprises a plurality of radial slots therein dividing the flange into wedge-shaped sections, said flange defining a hole having a first diameter, said body being mountable around the mutually defined exterior surfaces of said pair of upwardly extending members;

a post member having a second diameter which is greater than the first diameter and at least one annular recess having a third diameter which is less than the first diameter such that the post is axially positionable in said hole by inserting the post therethrough, causing the deflection of the inwardly directed slotted flange until the inwardly directed slotted flange seats in the annular recess of the post, thereby permitting the post and cylindrical body may rotate independently while the post is axially retained in the hole; and a corresponding threading for engaging the threading on the upwardly extending members.

5. The assembly as set forth in claim 4, wherein said sidewall of said cylindrical body has a reduced thickness at a circumferential junction of said inwardly directed flange such that said wedge-shaped sections may deflect resiliently.

6. An orthopaedic rod implant apparatus, comprising:

at least one rod;

at least one corresponding bone-to-rod coupling device having a head, said head including a pair of upwardly extending members defining therebetween a rod receiving channel, said upwardly extending members each having mutually defined exterior and interior surfaces a threading on one of said exterior and interior surfaces; and a unitary locking cap for securely locking said rod in said channel of said head of said bone-to-rod coupling device, said cap being mountable around the mutually defined exterior surfaces of said upwardly extending members, said cap including a cylindrical body having a sidewall having inner and outer surfaces, said inner surface including an annular recess, a first end, which is open, and a second end, said body being mountable around the mutually defined exterior surfaces of said pair of upwardly extending members;

a post member which is positionable between said mutually defined interior surfaces of said pair of upwardly extending members, said post member including a plurality of deflecting arms extending radially therefrom which seat in the annular recess of said cylindrical body such that the post and the cylindrical body may rotate independently, but such that the post may not be removed;

a corresponding threading for engaging the threading on the upwardly extending members.

7. An orthopaedic rod implant apparatus, comprising:

at least one rod;

at least one corresponding bone-to-rod coupling device having a head, said head including a pair of upwardly extending members defining therebetween a rod receiving channel, said upwardly extending members each having mutually defined exterior and interior surfaces a threading on one of said exterior and interior surfaces; and a unitary locking cap for securely locking said rod in said channel of said head of said bone-to-rod coupling device, said cap being mountable around the mutually defined exterior surfaces of said upwardly extending members, said cap including a cylindrical body having a sidewall having inner and outer surfaces, a first end, which is open, and a second end, said second end including an inwardly directed flange which comprises a plurality of radial slots therein dividing the flange into wedge-shaped sections, said flange defining a hole having a first diameter, said body being mountable around the mutually defined exterior surfaces of said pair of upwardly extending members;

a post member having a second diameter which is greater than the first diameter and at least one annular recess having a third diameter which is less than the first diameter such that the post is axially positionable in said hole by inserting the post therethrough, causing the deflection of the inwardly directed slotted flange until the inwardly directed slotted flange seats in the annular recess of the post, thereby permitting the post and cylindrical body may rotate independently while the post is axially retained in the hole; and a corresponding threading for engaging the threading on the upwardly extending members.

8. The assembly as set forth in claim 7, wherein said sidewall of said cylindrical body has a reduced thickness at a circumferential junction of said inwardly directed flange such that said wedge-shaped sections may deflect resiliently.

* * * * *